US00PP10521P

United States Patent [19]

Hunt et al.

[11] Patent Number: Plant 10,521

[45] Date of Patent: Jul. 28, 1998

[54] TERNSTROEMIA GYMNANTHERA 'GREWAD'

[75] Inventors: Marilyn Hunt, Wharton, Tex.; Grady Wadsworth, deceased, late of El Campo, Tex., by Judith K. Wadsworth, legal representative

[73] Assignee: Greenleaf Nursery Company, Park Hill, Okla.

[21] Appl. No.: 757,757

[22] Filed: Dec. 4, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Synnestvedt & Lechner

[57] ABSTRACT

A new variety of Japanese Ternstroemia plant, *Ternstroemia gymnanthera* 'Grewad', which is particularly characterized by its dark burgundy new foliage color during cool months and uniform, self-branched growth habit, and which is distinguishable from standard Japanese Ternstroemia plants which demonstrate variable color intenstiy of new foliage and an irregular branching habit.

7 Drawing Sheets

BACKGROUND OF THE NEW PLANT

The present invention relates to the discovery and asexual propagation of a new and distinct cultivar of *Ternstroemia gymnanthera*, a member of the Theaceae family that is commonly known as Japanese Ternstroemia, and often referred to as Cleyera. The new variety of *Ternstroemia gymnanthera* has benn given the cultivar name 'Grewad'.

The new variety was discovered by Grady Wadsworth in the early spring of 1988, amongst a cultivated planting of seedling Japanese Ternstroemia plants at Greenleaf Nursery in El Campo, Tex. The parent variety of Japanese Ternstroemia is unknown, as there is currently only one other named cultivar, *Ternstroemia gymnantheras* 'Variegata', in horticultural literature. The parent species is referred to herein as "standard" "traditional" Japanese Ternstroemia.

The new 'Grewad' plant was recognized as being very different in appearance from traditional Japanese Ternstroemia plants, and was particularly selected for its unique new foliage color, improved branching and compact growth habit. The botanical characteristics of the new 'Grewad' variety are substantially the same as the parent species, but for the distinctive dark burgundy-colored new foliage and uniformly self-branched, compact growth habit exhibited by the 'Grewad' plants. The distinctive dark burgundy color of the 'Grewad' plant's new foliage color particularly develops in late fall, winter, and early spring, whenever cool temperatures and favorable growing conditions coincide. The new 'Grewad' variety's distinctive color and uniform branching habit which responds well to shearing give it several desirable characteristics for ornamental landscape use. The new variety is readily distinguishable from traditional or standard Japanese Ternstroemia plants, which are extremely variable in the color intensity of new foliage and which demonstrate an irregular branching habit as it grows.

The new 'Grewad' variety was first asexually propagated by Marilyn Hunt in the summer of 1988 at the same nursery in which it was discovered. The new variety has shown to be stable in its distinguishing characteristics over several generations, through successive asexual propagations using vegetative cuttings.

BRIEF DESCRIPTION OF THE DRAWINGS

The accompanying photographic drawings illustrate in color the 'Grewad' cultivar as grown in a nursery in El Campo, Tex., and also show the comparison between the new 'Grewad' variety and the parent species, as well as the coloration of new and mature foliage on both the new and parent plants. Except as noted, the photographs are of plants grown outdoors and in containers above ground.

DETAILED DESCRIPTION OF THE NEW PLANT

Figure 1:
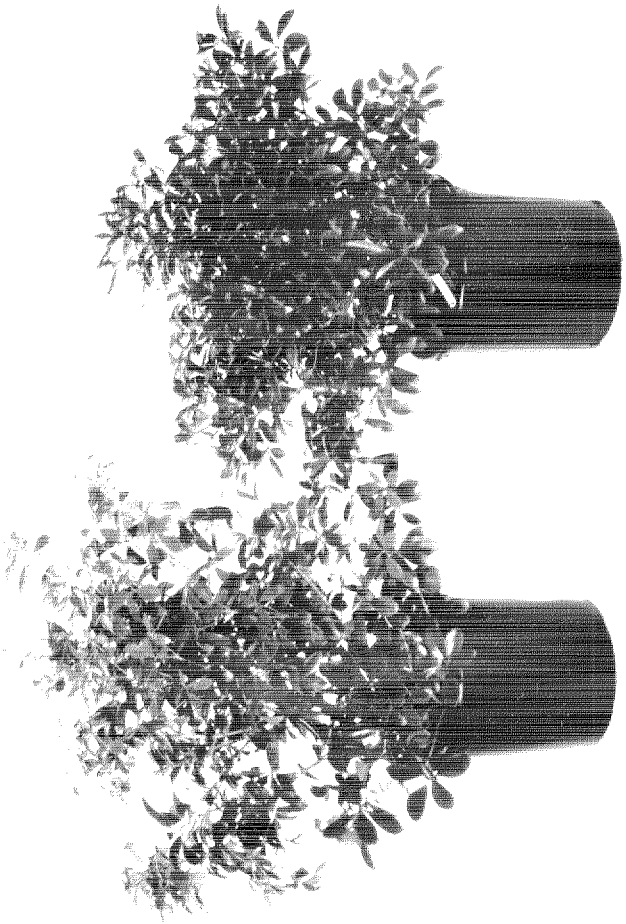
FIG. 1 shows a comparison between a traditional Japanese Ternstroemia plant (left) and the new 'Grewad' variety (right) in the spring. The two plants were grown under culturally identical conditions. Both plants received shearings to improve fullness and structure. The uniformity and symmetry of the 'Grewad' plant demonstrates how well its branching habit responds to shearing.
Figure 2:
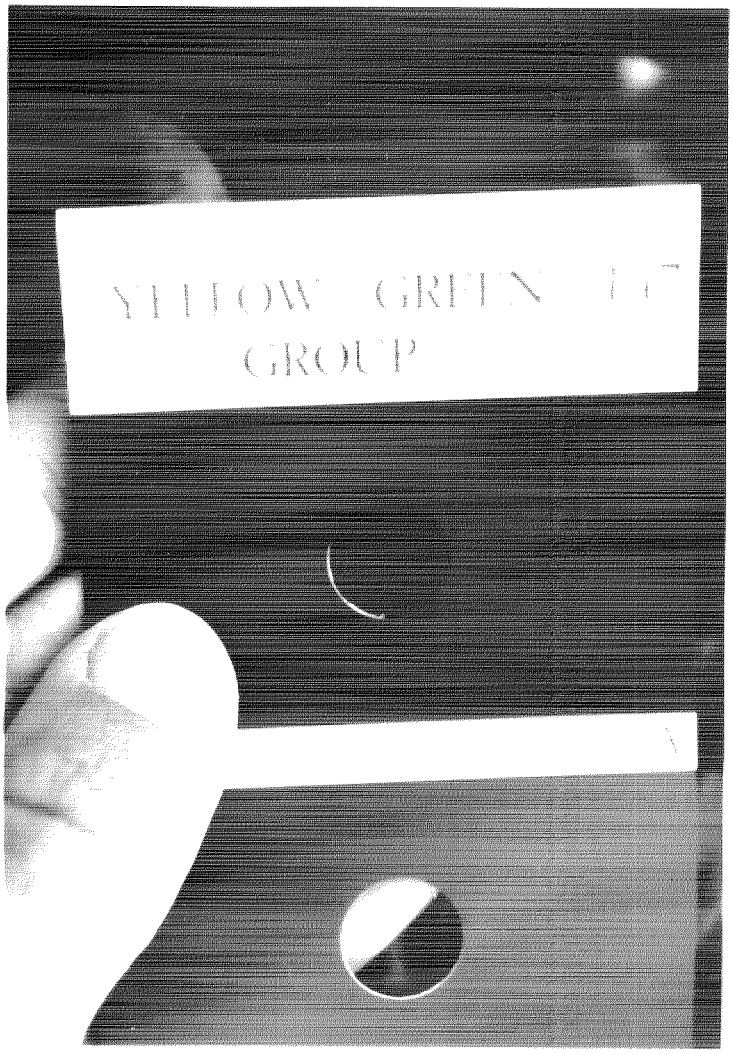
FIG. 2 shows the foliage of the new 'Grewad' variety.
Figure 3:
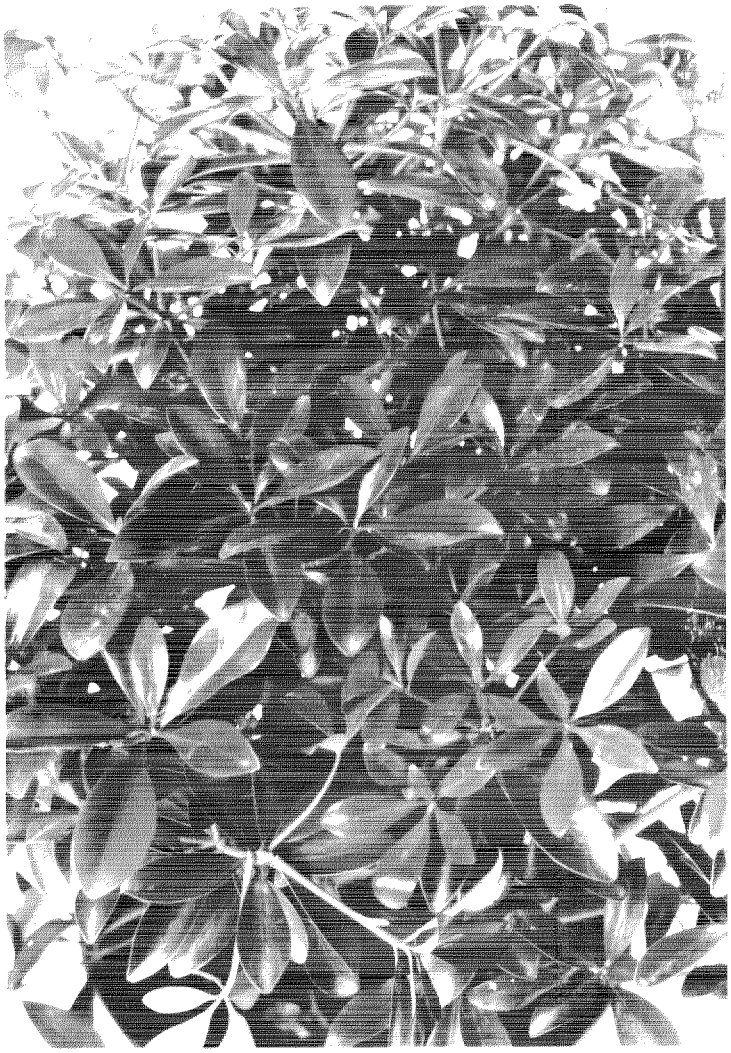
FIG. 3 shows a close-up of the foliage of the new 'Grewad' variety.
Figure 4:
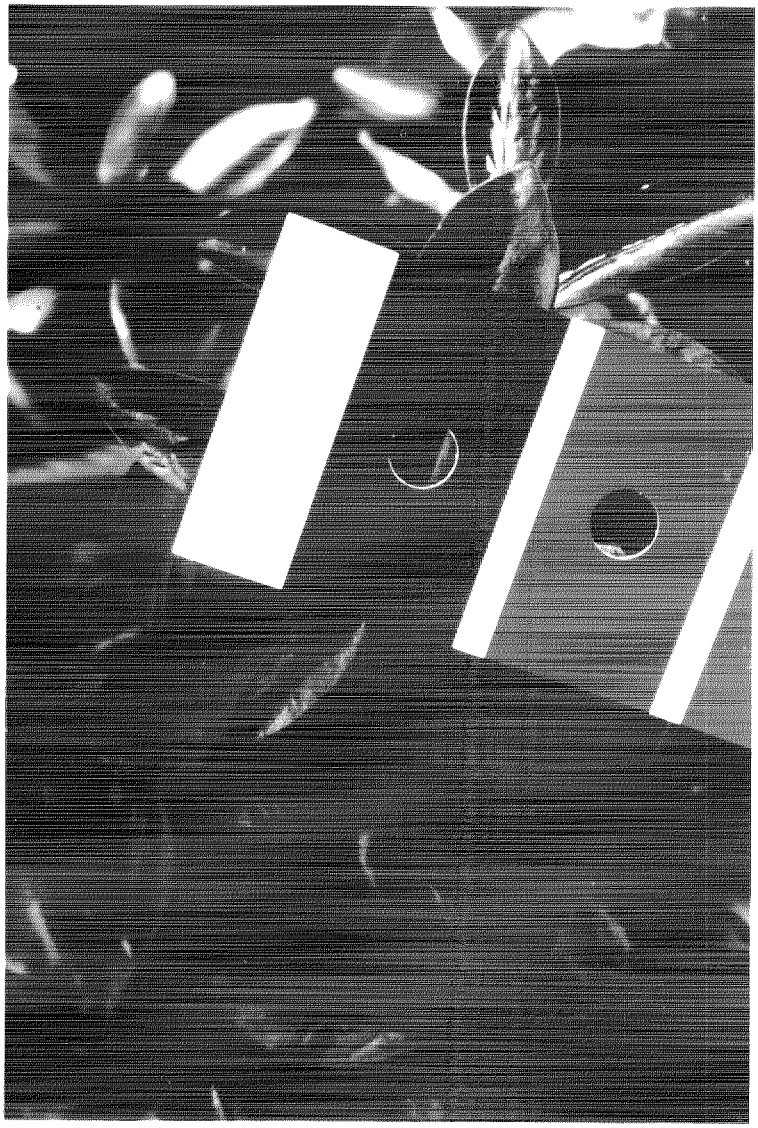
FIG. 4 shows the top side of immature foliage of the new 'Grewad' variety, superimposed by the matching R.H.S. color card of the Greyed-Purple Group.
Figure 5:
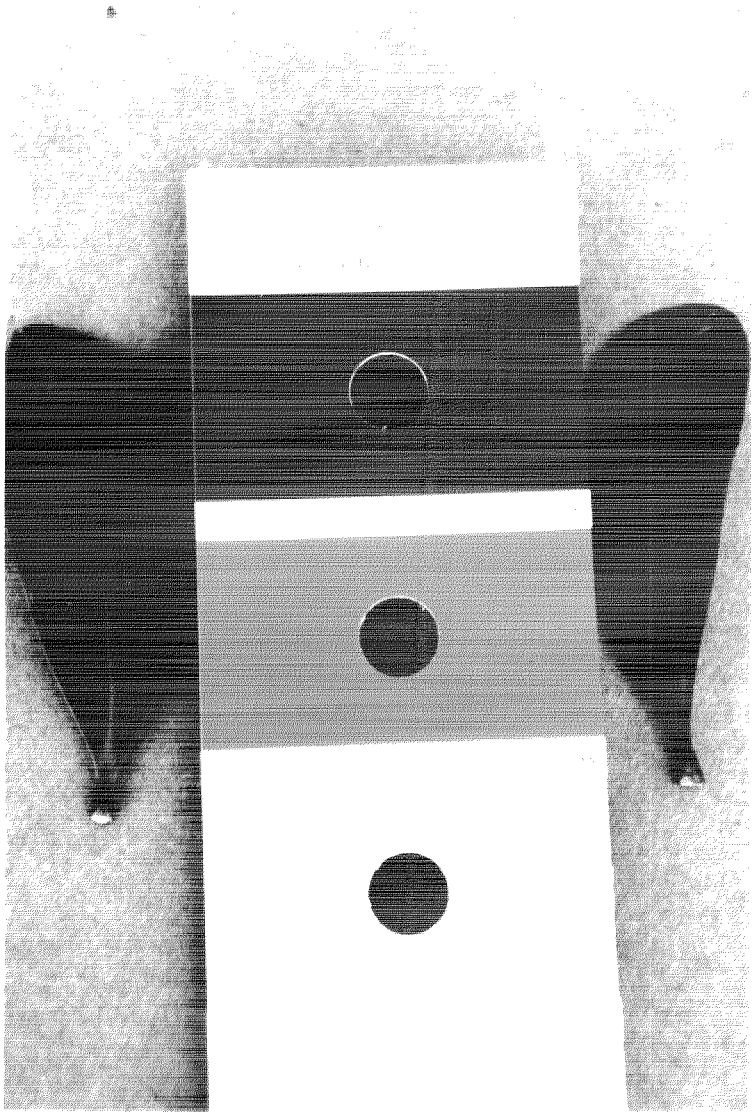
FIG. 5 shows the top side of mature foliage of the new 'Grewad' variety, superimposed by the matching R.H.S. color card of the Yellow-Green Group.
Figure 6:
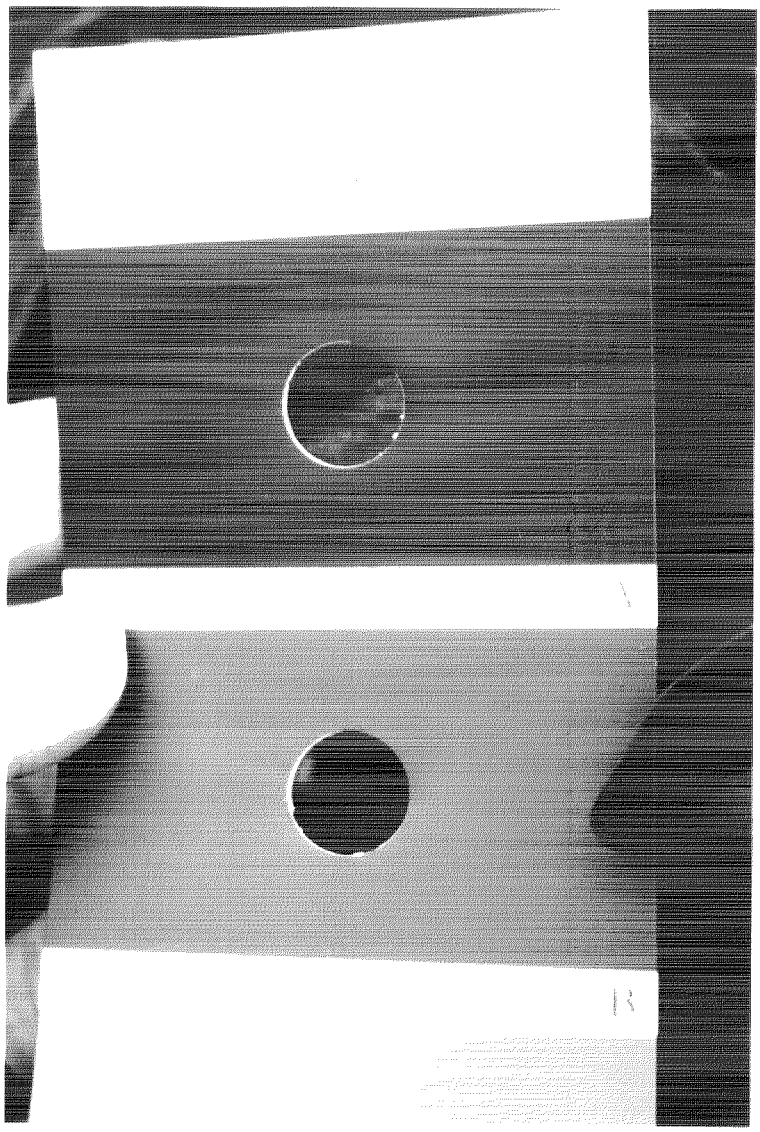
FIG. 6 shows the top side of immature foliage of a traditional Japanese Ternstroemia plant, superimposed by the matching R.H.S. color card of the Greyed-Orange Group.
Figure 7:
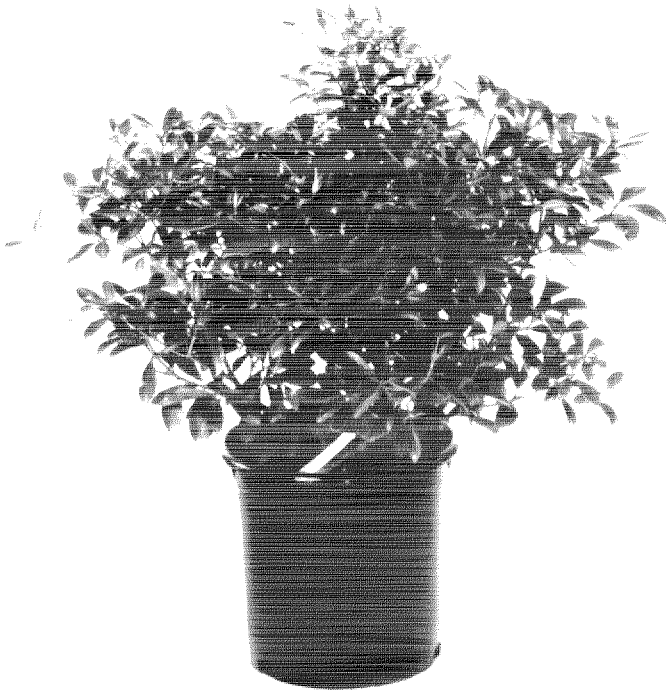
FIG. 7 shows the top side of mature foliage of a traditional Japanese Ternstroemia plant, superimposed by the matching R.H.S. color card of the Yellow-Green Group.

The following detailed description of the new *Ternstroemia gymnanthera* 'Grewad' plant is based upon observations made of the plants grown under commercial, wholesale nursery production practices and in landscape plantings in El Campo, Tex. It is believed that this description will apply to 'Grewald' cultivar plants grown in similar conditions of soil and climate elsewhere.

Throughout this specification, color names beginning with a small letter signify that the name of that color as used in common speech is aptly descriptive. Color names beginning with a capital letter designate color values based on the R.H.S. Colour Chart published by The Royal Horticultural Society of London, England.

Name: *Ternstroemia gymnanthera* 'Grewad'.

Origin: Seedling of unknown parentage.

Parentage: Unknown variety of *Ternstroemia gymnanthera* plants.

Hardiness: USDA Zone 7; typical of the species.

Growth habit: Upright-oval; uniform; denser of branching and canopy and more compact than the parent species.

Texture: Medium; denser of branching and canopy than the parent species.

Size: Mature height is anticipated to be about 2.5–3.0 m. with a width of about 1.5–2.0 m.; this is typically shorter than the parent species as a function of lesser terminal growth and denser branching as compared to the species; mature width of the plant is anticipated to be typical of the species.

Foliage:

*Type.*—Evergreen.

*Arrangement.*—Irregularly, spirally arranged around the apical end of the stem of each growth flush. The lower end of each stem is leafless with widely spaced blind leaf nodes. Leaf and blind leaf node spacing is similarly irregular on the 'Grewad' plants and the parent species. The number of branches per growth flush vary from about 1 to 7, which is similar to the parent species. However, the length of each growth flush is shorter than (about 30% as long as) the growth flushes of the parent species, thereby giving the plant a fuller appearance.

*Leaf insertion.*—Petiolate.

*Petiole length.*—About 5 mm. (same as parent species)

*Leaf shape.*—Elliptic to obovate/cuneate-obovate.

*Leaf tip.*—Retuse.

*Leaf base.*—Attenuate.

*Leaf margin.*—Entire.

*Leaf venation.*—Pinnate.

*Leaf surface above.*—Lustrous, leathery.

*Leaf surface below.*—Glabrous, leathery.

*Mature leaf length.*—About 65–70 mm.

*Mature leaf width.*—About 25–30 mm.

Flower: Typical of the species; perfect with fleshy petals white to cream in color; the corolla is about 8–10 mm. across and held on a 10–20 mm. peduncle produced singly from the leaf axils or blind leaf nodes on current growth; inconspicuous; flowers observed October/November, contrary to literature which refers to flowers observed in May/June.

Fruit: Not observed but expected to be typical of the species.

Color:

TABLE 1

| | 'Greward' | Standard Japanese Ternstroemia |
|---|---|---|
| New Foliage - Top: | Greyed-Purple 187A | Greyed-Orange 166A |
| New Foliage - Bottom: | Yellow-Green 146B | Yellow-Green 146D |
| Mature Foliage - Top: | Yellow-Green 147B | Yellow-Green 147A |
| Mature Foliage - Bottom: | Yellow-Green 146B | Yellow-Green 147C |
| Mature Stem: | Brown 200B | Brown 200B |

It is claimed:

1. A new and distinct cultivar of *Ternstroemia gymnanthera* named 'Grewad', as herein illustrated and described.

* * * * *